US00PP22290P2

(12) United States Plant Patent
Hardy et al.

(10) Patent No.: US PP22,290 P2
(45) Date of Patent: Nov. 29, 2011

(54) ***GAURA* PLANT NAMED 'HARROSY'**

(50) Latin Name: *Gaura lindheimeri*
Varietal Denomination: Harrosy

(76) Inventors: Rob Hardy, Whitchurch (GB); Rosy Hardy, Whitchurch (GB)

( * ) Notice: Subject to any disclaimer, the term of this patent is extended or adjusted under 35 U.S.C. 154(b) by 0 days.

(21) Appl. No.: 12/804,236

(22) Filed: Jul. 16, 2010

(51) Int. Cl.
*A01H 5/00* (2006.01)

(52) U.S. Cl. ..... Plt./432

(58) Field of Classification Search ..... Plt./432
See application file for complete search history.

(56) References Cited

OTHER PUBLICATIONS

UPOV-ROM PBR 20072908 published Feb. 15, 2008, one page.*

* cited by examiner

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of *Gaura lindheimeri*, 'HARROSY', characterized by its flowers that emerge from crimson red buds and have flower petals that are white in color with pink margins.

2 Drawing Sheets

Botanical classification: *Gaura lindheimeri.*
Cultivar designation: 'HARROSY'.

BACKGROUND OF THE INVENTION

The present invention relates to a new and distinct cultivar of *Gaura* plant, botanically known as *Gaura lindheimeri* 'HARROSY' and will be referred to hereafter by its cultivar name, 'HARROSY'.

The Inventors discovered the new cultivar, 'HARROSY' as a branch mutation of *Gaura lindheimeri* 'Siskiyou Pink' (not patented) in a garden plot at their nursery in Whitchurch, Hants, United Kingdom in summer of 2006.

Asexual reproduction of the new cultivar was first accomplished by softwood stem cuttings in Whitchurch, Hants, United Kingdom in 2006 under the direction of the Inventors. Propagation has determined that the characteristics of this cultivar are stable and are reproduced true to type in successive generations.

SUMMARY OF THE INVENTION

The following traits have been repeatedly observed and represent the characteristics of 'HARROSY'. These attributes in combination distinguish 'HARROSY' as a new and distinct cultivar of *Gaura.*

1. 'HARROSY' exhibits flowers that have petals that are white in color with pink margins.
2. 'HARROSY' exhibits flower buds that are crimson red in color.

'HARROSY' can be most closely compared to its parent plant, 'Siskiyou Pink'. 'Siskiyou Pink' differs from 'HARROSY' in having flowers with petals that are pink in color rather than white with pink margins as observed for 'HARROSY'. 'HARROSY' can also be compared to plants of the species, *Gaura lindheimeri*, which differ from 'HARROSY' in having white flowers and to the cultivar 'Sunny Butterflies' (not patented), which differs from 'HARROSY' in having flower petals that are pink in color with a white edge.

BRIEF DESCRIPTION OF THE DRAWING

The accompanying colored photographs illustrate the overall appearance and distinct characteristics of the new *Gaura*. The photographs were taken of six month-old plants of 'HARROSY' as grown outdoors in 12-cm containers in Whitchurch, Hants, United Kingdom.

The photograph in FIG. 1 is a view of flowering stems of 'HARROSY'.

Figure 1:
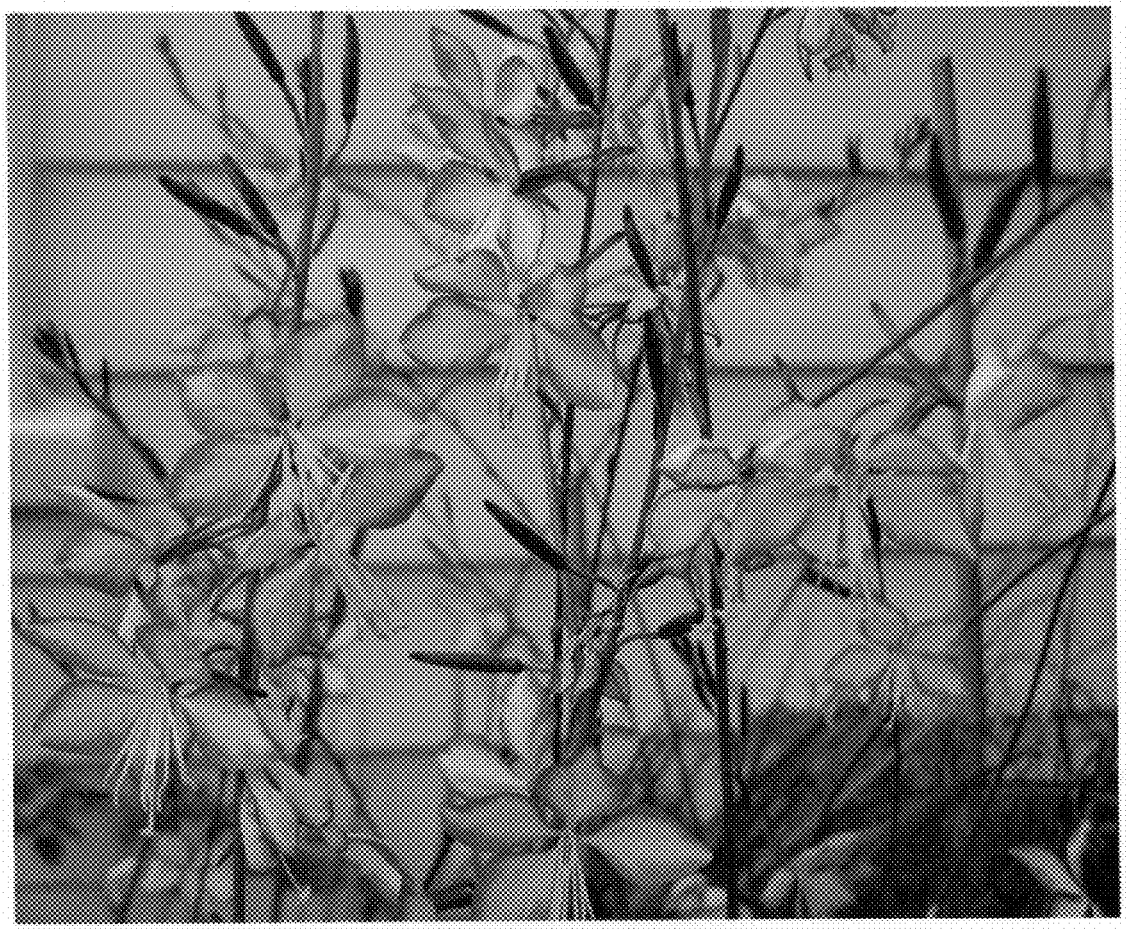
Figure 2:
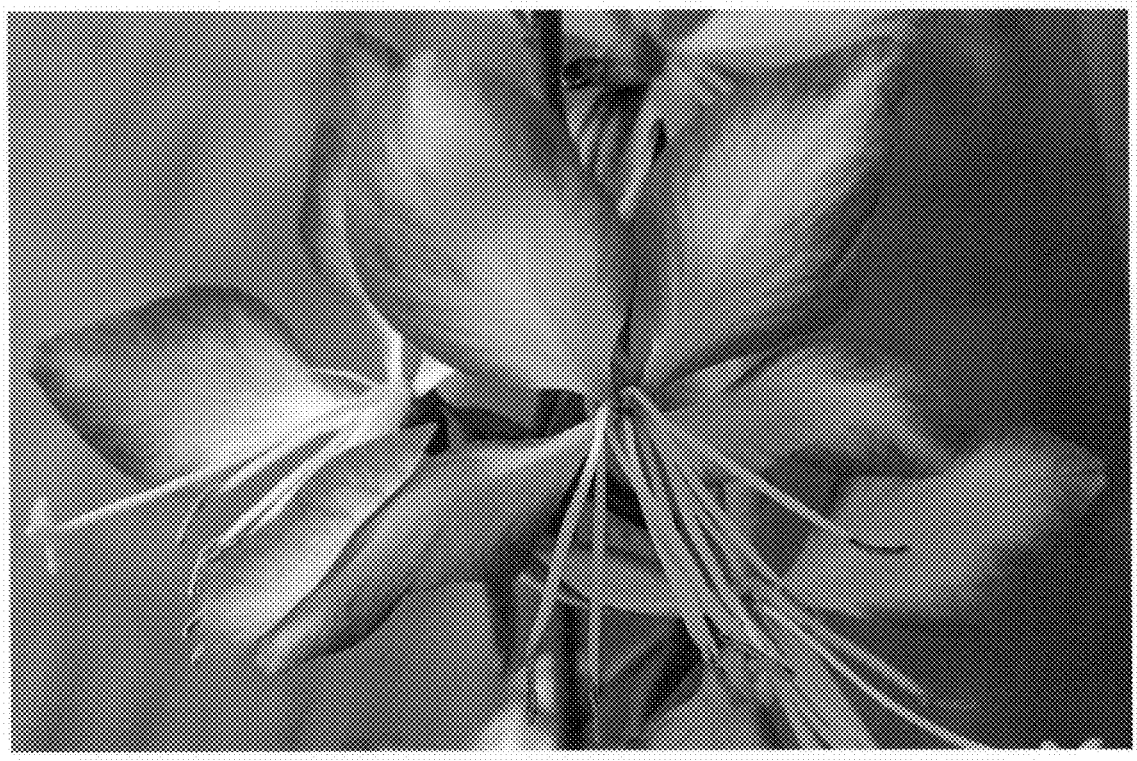
Figure 3:
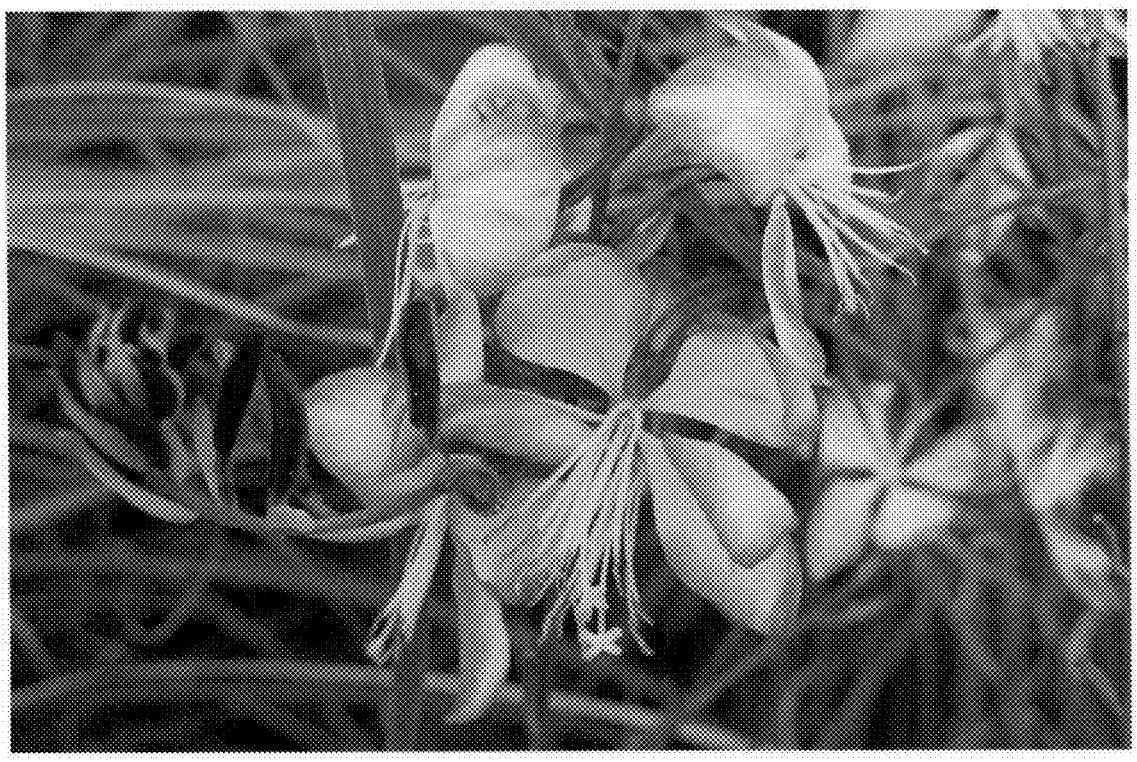

The photograph in FIG. 2 provides a close-up view of a flower of 'HARROSY' while the photograph in FIG. 3 provides a view of flowers and flower buds of 'HARROSY'. The colors in the photographs are as close as possible with digital photography techniques available, the color values cited in the detailed botanical description accurately describe the colors of the new *Gaura.*

DETAILED BOTANICAL DESCRIPTION OF THE PLANT

The following is a detailed description of six month-old plants of the new cultivar as grown outdoors in 12-cm containers in full sun in Whitchurch, Hants, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Botanical classification: 'HARROSY' is a cultivar of *Gaura lindheimeri.*

Parentage: Branch mutation of *Gaura lindheimeri* 'Siskiyou Pink'.

General characteristics:

*Blooming period.*—Late July to September in southern UK.

*Plant habit.*—Herbaceous perennial, semi-upright habit.

*Height and spread.*—Reaches about 80 cm in height and about 60 cm in width.

*Cold hardiness.*—U.S.D.A. Zone 2.

*Diseases and pests.*—No susceptibility or resistance to diseases or pests has been observed.

*Root description.*—Fibrous roots.

*Branching habit.*—Freely branched, about 30 branches per plant emerging at 45° angles from main stem.

Growth and propagation:

*Growth rate.*—Moderate.

*Propagation.*—Softwood stem cuttings.

*Time required for root initiation.*—10 days under mist at 10 to 12° C.

*Time required for root development.*—About 10 weeks from rooted cutting to 2 L container commercial size.

Stem description:

*Stem size.*—45 to 60 cm in length and 2 mm in width, stems are solid.

*Stem shape.*—Round.

*Stem color.*—138A.

*Stem surface.*—Pubescent.

*Internode length.*—Average of 4 cm, ranging between 3 to 6 cm in length.

Foliage description:

*Leaf shape.*—Lanceolate to oblanceolate.

*Leaf division.*—Simple.

*Leaf base.*—Sessile.

*Leaf apex.*—Obtuse to acute.

*Leaf venation.*—Pinnate, 138B in color on upper and lower surfaces.

*Leaf margins.*—Entire, occasionally shallowly dentate.

*Leaf attachment.*—Sessile.

*Leaf arrangement.*—Alternate.

*Leaf surface.*—Upper and lower surface pubescent.

*Leaf color.*—138A in color on upper and lower surfaces.

*Leaf size.*—Average of 6.5 cm in length and 1.3 cm in width.

Flower description:

*Inflorescence type.*—Terminal spike.

*Lastingness of flowers on the plant.*—About 3 days, self cleaning.

*Inflorescence height.*—20 to 30 cm. Inflorescence diameter: 5.0 cm.

*Flower type.*—Single.

Flower size.—Average of 4.4 cm in height and 2.5 cm in diameter.

*Flower fragrance.*—None.

*Flower number.*—Average of 25 per branch.

*Flower aspect.*—45° to 60° angle from peduncle.

*Flower bud.*—Narrowly ellipsoid with a slightly swollen base, 1.8 cm in length, 3 mm in width, 60C in color.

*Petals.*—4 per flower, lanceolate in shape, rotate, smooth, acute apex, attenuate base margins entire, about 2.0 cm in length and 1.1 cm in width, NN155D in color with margins (1 to 5 mm in width) 67B in color with feathering toward the center on both the upper and lower surfaces.

*Sepals.*—4 per flower, linear in shape, strongly reflexed, 1.7 cm in length, 2 mm in width, fused at base acute apex, margins entire, involute, surface sparsely pubescent, 185A in color on both the upper and lower surfaces.

*Bract.*—Narrowly elliptic in shape, 7 mm in length and 2 mm in width, 138B in center and with margins 150D in color when flowers fully open, 178A in color when flowers in buds.

*Peduncle.*—Round, sparsely pubescent, 20 to 30 cm in length and 1 mm in width, 138A in color.

*Pedicels.*—1.2 cm in length, 1.0 mm in width and 138A in color.

Reproductive organs:

*Gynoecium.*—1 pistil, stigma; 4-lobed, 2 mm in diameter, each lobe 1 mm in length, 150D in color, style; cylindrical in shape, 2.3 cm in length and 1 mm in width, NN155D in color, ovary; inferior, 4-angled, sparsely pubescent surface, about 5 mm in length and 1 mm in width, N144D in color.

*Androecium.*—8 stamens, anthers; dorsifixed, linear-oblong in shape, 3 mm in length, <1 mm in width, and 175D in color, filament; 1.2 cm in length, <1 mm in width and NN155D in color, pollen; low in abundance and 11D in color.

*Fruit.*—Ovoid woody capsule.

*Seeds.*—3 to 4 seeds per fruit 3 mm in length, 1 mm in width, 176C in color.

It is claimed:

1. A new and distinct cultivar of *Gaura* plant named 'HARROSY' as herein illustrated and described.

* * * * *